United States Patent [19]

Sergienko et al.

[11] Patent Number: 5,030,790

[45] Date of Patent: Jul. 9, 1991

[54] PROCESS FOR PRODUCING BUTENE-1

[76] Inventors: Galina S. Sergienko, ulitsa Rabochaya, 64, kv. 43, Grozny, U.S.S.R.; Viktor I. Zhukov, ulitsa Neftezavodskaya, 4, kv. 1., Grozny, U.S.S.R.; Gennady P. Belov, Shkolnv bulvar, 5, kv. 53, Moskovskaya oblast, Chernogolovka, U.S.S.R.; Fridrikh S. Dyachkovsky, ulitsa Kosvgina, 6, kv. 9, Moscow, U.S.S.R.; Sergei S. Ivanchev, ulitsa Nalichnaya, 36, kv. 37, Leningrad, U.S.S.R.; Anatoly I. Germashev, kvartal 175A,6, kv. 5, Stavropolsky krai, Budennovsk, U.S.S.R.; Jury M. Petrov, mikroraion, 7,17, kv. 37, Stavropolsky krai, Budennovsk, U.S.S.R.; Valery I. Lazutin, ulitsa Timiryazeva, 77, Grozny, U.S.S.R.; Valery A. Yatsenko, prospekt Lenina, 117, kv. 85, Grozny, U.S.S.R.; Malik S. Gabutdinov, ulitsa Okolnaya, 94A, korpus 2, kv. 41., Kazan, U.S.S.R.

[21] Appl. No.: 332,275

[86] PCT. No.: PCT/SU88/00129
§ 371 Date: Mar. 10, 1989
§ 102(e) Date: Mar. 10, 1989

[22] PCT Filed: May 26, 1989

[30] Foreign Application Priority Data

Jul. 13, 1987 [SU] U.S.S.R. .............................. 4267266

[51] Int. Cl.$^5$ ............................................. C07C 2/24
[52] U.S. Cl. ................................... 585/513; 585/512; 585/522; 585/524
[58] Field of Search ................. 885/512, 513, 522, 524

[56] References Cited

U.S. PATENT DOCUMENTS

| | | | |
|---|---|---|---|
| 3,482,000 | 12/1969 | Fernalo et al. .................... | 585/522 |
| 3,557,236 | 3/1967 | Presswood et al. ............... | 585/522 |
| 3,558,494 | 1/1971 | Gourlaoven et al. .............. | 585/522 |
| 3,751,518 | 8/1973 | Hagan et al. ..................... | 585/522 |
| 3,879,485 | 4/1975 | Belov et al. ...................... | 585/512 |
| 4,000,211 | 12/1976 | Smith et al. . | |
| 4,532,370 | 7/1985 | Le Quan et al. .................. | 585/524 |
| 4,615,998 | 10/1986 | Le Quan et al. .................. | 585/512 |
| 4,786,717 | 11/1988 | Bretches et al. .................. | 556/187 |

FOREIGN PATENT DOCUMENTS

| | | | |
|---|---|---|---|
| 0135441 | 3/1985 | European Pat. Off. ............ | 585/512 |
| 2552079 | 3/1985 | France . | |
| 2581381 | 11/1988 | France . | |
| 0455082 | 4/1975 | U.S.S.R. ............................ | 585/512 |
| 459451 | 4/1975 | U.S.S.R. . | |
| 0496258 | 4/1976 | U.S.S.R. ............................ | 585/512 |
| 0681034 | 8/1979 | U.S.S.R. ............................ | 585/512 |
| 187822 | 12/1981 | U.S.S.R. . | |
| 1123474 | 8/1968 | United Kingdom ............... | 585/512 |
| 1153519 | 5/1969 | United Kingdom ............... | 585/513 |

OTHER PUBLICATIONS

"Dimerization and DIS Proportionation of Olefines", by V. Sh. Fieldblume, 1978, Khimiya Publishers, Moscow, p. 38.

"Dimerization of Ethylene", by Matkovsky et al., Kinetika i Kataliz, vol. 19, Issue 1, 1978, p. 263.

Primary Examiner—Patrick P. Garvin
Assistant Examiner—James Saba
Attorney, Agent, or Firm—Fleit, Jacobson, Cohn, Price, Holman & Stern

[57] ABSTRACT

The production of butene-1 is effected by way of dimerization of ethylene in the presence of a catalytical system: titanium tetralakoxide-aluminium trialkyl in a hydrocarbon solvent, followed by rectification of the reaction mass formed in the dimerization in the presence of a compound selected from the group consisting of aliphatic mono- and dihydric alcohols, aliphatic ethers, cyclic ethers, aliphatic ketones, amides of carboxlic acids.

3 Claims, No Drawings

PROCESS FOR PRODUCING BUTENE-1

FIELD OF THE ART

The present invention relates to the chemical and petrochemical industries and, more particularly, to a process for producing butene-1.

PRIOR ART

Known in the art is a process for dimerization of ethylene catalyzed by a system diisobutylaluminium chloride-nickel oleate under different conditions with the production of butene-1. The maximum content of butene-1 in the resulting dimerizate is 59.1% mass and its composition is the following: trans-butene-1—1–23.9% by mass, cis-butene-2—12.0% by mass, butene-1—59.1% by mass, n-butene—5% by mass. In practicing of the process the selectivity with respect to butene-1 is low and a great number of side products such as butenes-2 are formed in the dimerizate, whereas for the processes of polymerization and copolymerization butene-1 containing at most 0.2% by mass of butenes-2 is required (cf.V.Sh.Fieldblume, "Dimerization and DIS Proportionation of Olefines", 1978, "Khimiya" Publishers, Moscow, p. 38).

Also known in the art is a process for dimerization of olefines in the presence of a catalyst which comprises nickel complexes supported on a solid carrier composed of $SiO_2$, alumosilicate or a mixture of both. The resulting dimerizate consists of 70% by mass of butene-1 and 30% by mass of butenes-2 (U.S. Pat. No. 4,000,211).

In practicing of this process an expensive catalyst is used, the selectivity with respect to butene-1 is low and a high content of butenes-2 is present in the resulting dimerizate.

Known in the art is the production of butene-1 by way of dimerization of ethylene catalyzed by titanium alkoxide $Ti(OR)_4$, aluminium trialkyl $AlR_3$ in a medium of ethers. (See Kinetika i Kataliz, vol. 19, iss. 1, 1978; P. E. Matkovsky et al. "Dimerization of Ethylene", p. 263).

However, the use of ethers as the reaction medium is inapplicable on a commercial scale due to their high costs and a strong narcotic effect.

Furthermore, in the production of butene-1 by way of dimerization of ethylene on a catalytical system $Ti(OR)_4$-$AlR_3$ there are encountered, first of all, the problem of recovering butene-1 from a mixture of products formed in the dimerization of ethylene (butene-1, hexenes, octenes, polymer, catalyst) and, especially, the problem of separation and isolation of the catalyst which can be fully soluble in the reaction mixture. In this case two procedures can be used:

(1) the removal of the catalyst prior to distillation of hydrocarbons either by lowering solubility and filtration or centrifugation, or by way of a two-phase extraction, for example, with water;

(2) straight distillation of hydrocarbons (nonconverted ethylene, butene-1, hexenes and other oligomers) at which the catalyst remains at the bottom of the distillation apparatus; it is still soluble, but concentrated in oligomers (CS, B, 187822).

From the economic standpoint this procedure is preferable since it enables elimination of an intermediate stage of the two-phase washing or separation of solid particles; the residue is obtained in a small amount and it can be readily removed, e.g. by calcination.

At the same time, it has been noticed in practice that during evaporation a rather elevated temperature is maintained in order to obtain the most effective concentration of the catalyst; however, this elevated temperature causes secondary reactions of isomerization and polymerization of butene-1.

Also known in the art is a process, wherein butene-1 is obtained by way of dimerization of ethylene in the presence of a catalytical system $Ti(OC_4H_9)$—$AlR_3$ upon a continuous supply of ethylene, a hydrocarbon solvent and solutions of the catalyst components in a hydrocarbon solvent (FR, B, No. 2581381).

The reaction mass withdrawn from the reactor is delivered to fractionation (distillation or rectification).

In a commercial implementation of this process the quality of butene-1 is gradually reduced due to the formation of butene-2. The latter appears as a result of fractionation due to isomerization of butene-1 on the products of the catalytical system. The higher the temperature in the rectification or distillation column, the longer is the average residence time of the reaction mass in the column, the more intensive is the process of isomerization, the higher is the content of butene-2 in butene-1. At a temperature within the range of from 90° to 120° C. the content of butene-2 in butene-1 can vary from 1 to 4% by volume which does not meet the requirements imposed on the raw materials employed in processes of homo- and copolymerization.

To partly inhibit the reaction of isomerization of butene-1 into butene-2, prior to the beginning of rectification the reaction mixture is added with a modifying agent selected from the class of amines such as cyclohexylamine, 2-ethylhexylamine, dimbutylamine. The amount of the added amine is varied within the range of the molar ratio between the amine and titanium (contained in the reaction mixture) of from 0.1:1 to 10:1, preferably from 0.3:1 to 2:1.

The use, as the modifying agents, of amines—i.e. compounds which are, as a rule, very toxic (maximum allowable concentrations for the overwhelming majority of amines mentioned in FR, B, No. 2581381, are far below 10 $mg/m^3$) hinders a wide-scale commercial application of this process.

DISCLOSURE OF THE INVENTION

The present invention is directed to the provision, by selecting a new class of compounds employed as modifying agents inhibiting the reaction of isomerization of butene-1 into butene-2, of such a process for producing butene-1 which would make it possible to obtain the desired product of a higher purity while using less toxic compounds.

This object is accomplished by that in a process for producing butene-1 comprising dimerization of ethylene in the presence of a catalytical system titanium tetraalkoxide-aluminium trialkyl in a hydrocarbon solvent, followed by rectification of the reaction mass in the presence of a modifying agent, according to the present invention as the modifying agent use is made of a compound selected from the group consisting of aliphatic mono- or dihydric alcohols, aliphatic ethers or cyclic ethers, aliphatic ketones, amides of carnoxylic acids.

Owing to the present invention it has become possible to increase the purify of the resulting butene-1 by 2.0–9.3 times as compared to the desired product obtained by the process of FR, B, No. 2581381 while avoiding the use of toxic compounds.

According to the present invention, it is advisable, when using aliphatic mono- or dihydric alcohols, or aliphatic cyclic ethers, or aliphatic ketones as the modifying agent, to carry out the rectification at a molar ratio of the modifying agent to the aluminium trialkyl of the catalytical system equal to 1-3.

The present invention enables the production of butene-1 using compounds with a maximum allowable concentration within the range of from 200 to 500 mg/m$^3$.

To perform the process in the presence of less volatile compounds according to the present invention, it is advisable, when using amides of carboxylic acids as a modifying agent, to carry out the rectification at a molar ratio of the modifying agent to aluminium trialkyl of the catalytical system ranging from 0.25 to 3.00.

BEST WAY OF CARRYING THE INVENTION INTO EFFECT

Further objects and advantages of the present invention will now become more fully apparent from the following detailed description of the process for producing butene-1 and examples illustrating this process.

The process for producing butene-1 according to the present invention consists in the following steps:
catalytic dimerization of ethylene;
deactivation of the catalyst;
recovery of butene-1 from the products of dimerization of ethylene.

The stage of the catalytical dimerization of ethylene is conducted in a reactor provided with a mechanical stirrer or not having it and comprises: continuous or discontinuous supply, into the reactor, of solutions of the catalyst components or a mixture thereof in a hydrocarbon solvent, a continuous supply of ethylene, a discontinuous withdrawal of the dimerization products from the reactor.

As the catalyst use is made of a bicomponent catalytical system consisting of compounds of titanium tetralkoxide of the general formula $Ti(OR)_4$ and aluminium trialkyl of the general formula $AlR'_3$, wherein R and R' are alkyl radicals containing 1 to 6 carbon atoms.

The molar ratio of the components of the catalyst $AlR'_3$ to $Ti(OR)_4$ can be varied within the range of from 1 to 100, but preferably, it should be maintained at 2.5-4:1. As a rule, these compounds are employed in the form of diluted solutions. As the solvent for them, use can be made of aliphatic hydrocarbons (butene, pentane, hexane, heptane), aromatic hydrocarbons (benzene, toluene), or olefines (butene-1, pentenes, hexenes) or mixtures thereof.

The stage of the catalytic dimerization of ethylene is conducted at a temperature within the range of from 20° to 100° C., preferably from 50° to 80° C.

The time of residence of the catalyst in the reactor can be varied from several minutes to several hours depending on the conditions of the dimerization stage.

The products of dimerization of ethylene formed in the reactor are withdrawn therefrom together with the solvent into an intermediate vessel, wherein the catalyst is deactivated by way of adding, to the reaction mixture, of the modifying agents according to the present invention (aliphatic mono- or dihydric alcohols, aliphatic or cyclic ethers, aliphatic ketones or amides of carboxylic acids).

Such deactivation ensures inhibition of the reaction of isomerization of butene-1 into butene-2 at the subsequent stage of recovering butene-1 from the reaction mixture. The recovery of butene-1 (rectification) can be carried out in a rectification column, the temperature in the column still being maintained within the range of from 80° to 100° C.

As the monohydric alcohol use can be made of ethanol, propanols, butanols, amyl alcohol, preferably isopropanol (the maximum allowable concentration is 10-150 mg/m$^3$).

As the dihydric alcohol use can be made of, for example, diethylene glycol, butanediol (maximum allowable concentration is 260-500 mg/m$^3$), as well as ethers of dihydric alcohols such as diethylene glycol dimethylate (maximum allowable concentration 80 mg/m$^3$).

As the ethers use can be made of, for example, diethyl ether, isopropyl ether, diisoamyl ether, the latter being preferable.

As cyclic ethers use can be made of, for example, tetrahydrofuran, dioxane (maximum allowable concentration is 10 to 100 mg/m$^3$).

As the ketones use can be made of, for example, methylethylketone, acetone (maximum allowable concentration is 200 mg/m$^3$).

As the amides of carboxylic acids use can be made of, for example, dimethylformide (maximum allowable concentration—10 mg/m$^3$).

From practical considerations, it is advisable to select modifying agents with a relatively low tension of vapors at the rectification temperature (90° to 150° C.).

In accordance with the present invention the modifying agent is used in such an amount that its maximum molar ratio to aluminium trialkyl $AlR_3$ contained in the reaction mass be not more than 3.

The minimum molar ratio between the modifying agent and $AlR_3$ (when using mono- and dihydric alcohols, ethers or cyclic ethers, ketones) is equal to 1 or (when using amides of carboxylic acids) to 0.25.

When the components are present in the reaction mass supplied to deactivation in a smaller than the above-specified lower limit, the content of butene-2 in butene-1 is not reduced. It is inadvisable to maintain the ratio between the components above the upper limit according to the present invention, since no further improvement of the quality of butene-1 is attained. This is due to the fact that upon introduction of the modifying agent in amounts non-ensuring the minimum ratio according to the present invention free aluminium trialkyl is still present in the reaction mass which, upon reaction with the titanium-containing component of the catalyst at an elevated temperature, forms active centers contributing to isomerization of butene-1 into butene-2. Upon introduction of the modifying agent in an amount ensuring the ratio above the one according to the present invention, no further improvement in the purity of butene-1 is reached, since the probability of origination of the isomerization centers is reduced to zero already at the upper limit value of 3 and a further increase of this value will result only in overrated consumption of the modifying agent and in increased costs of the production of butene-1.

The use of the modifying agents according to the present invention in the above-specified proportions relative to the aluminium trialkyl improves the purity of the recovered butene-1 by 2.0-9.3 times (at the account of inhibition of the reaction of isomerization of butene-1 into butene-2).

Furthermore, the use of the compounds according to the present invention as modifying agents provides the following additional advantages: due to a lowered rate of consumption of butene-1 in the reaction of its isomerization into butene-2 the yield of butene-1 upon its fractionation is naturally increased; the toxicity of the production is lowered, since the employed modifying agents are less toxic (by 3 to 10 and more times) as compared to the modifying agents (amines) employed in the process disclosed in FR, B, No. 2581381.

For a better understanding of the present invention, some specific examples are given herein below by way of illustration.

EXAMPLE 1

Solutions of $Ti(OC_4H_9)_4$ and $Al(i-C_4H_9)_3$ in pentane, a solvent (pentane) and ethylene are continuously fed into a 0.5 m$^3$ reactor. The catalyst concentration is 1 g/l. The reaction of dimerization is conducted at the temperature of 50° C. The reaction mass withdrawn from the reactor is supplied to distillation after a preliminary addition thereto of isopropanol in the ratio of 1 mol per mol of $Al(C_4H_9)_3$ present in the reaction mass. The distillate obtained after such distillation has the following composition, %: ethylene-9.96, butane—0.42, butene-1—81.56, butene-2—0.44, hexenes—5.53, the solvent—2.09.

EXAMPLES 2 THROUGH 10

Butene-1 is produced in a manner similar to that described in the foregoing Example 1. However, the reaction mass is subjected to rectification in the presence of methylethyl-ketone (Examples 2, 3 and 4), (isoamyl alcohol (Examples 5 and 6), diethylene glycol Example 7, ethylene glycol (Example 8) acetamide (Example 9), benzamide (Example 10).

The composition of the distillate after rectification is shown in Table 1 hereinbelow.

EXAMPLE 11

Butene-1 is produced in a manner similar to that of Example 1, except that use is made of $Al(i-C_4H_9)_3$ and into the reaction mass withdrawn from the reactor isopropanol is added in the ratio of 3 mol of the alcohol per mole of $Al(i-C_4H_9)_3$. The distillate after such distillation has the following composition, %: ethylene—10.5, butane—0.40, butene-81.76, butene-2—0.24, hexenes—5.10, the solvent—2.0.

EXAMPLE 12

Butene-1 is produced in a manner similar to that described in Example 1, except that into the reaction mass withdrawn from the reactor diethylene glycol is introduced in the ratio of 1 mole per mole of $Al(C_2H_5)_3$. The distillate composition after the distillation is the following, %: ethylene—10.1, butane—0.45, butene-1—81.50, butene-2—0.50, hexenes—5.75, the solvent—1.98.

EXAMPLE 13

Butene-1 is produced in a manner similar to that of Example 11, except that into the reaction mass withdrawn from the reactor diethylene glycol is introduced in the ratio of 3 moles per mole of $Al(i-C_4H_9)_3$. The composition of the distillate after the distillation is the following, %: ethylene—10.0, butane—0.45, butene-1—81.80, butene-2—0.20, hexenes—5.55, the solvent—2.0.

EXAMPLE 14

Butene-1 is produced in a manner similar to that described in Example 1, except that into the reaction mass withdrawn from the reactor diisoamyl ether is added in the ratio of 1 mole per mole of $Al(C_2H_5)_3$. After the distillation the composition of the distillate is the following, %: ethylene—9.98, butane—0.41, butene-1—81.61, butene-2—0.49, hexenes—5.43, the solvent—2.08.

EXAMPLE 15

Butene-1 is produced as described in Example 1, except that into the reaction mass withdrawn from the reactor diisoamyl ether is introduced in the ratio of 3 moles per mole of $Al(C_2H_5)_3$. The composition of the distillate after the distillation is the following, %: ethylene—9.96, butane—0.42, butene-1—81.67, butene-2—0.15, hexenes—5.51, the solvent—2.29.

EXAMPLE 16

Butene-1 is produced as in Example 2, except that into the reaction mass withdrawn from the reactor dioxane is introduced in the ratio of 1 mole per mole of $Al(i-C_4H_9)_3$. After the distillation the distillate has the following composition, %: ethylene—9.90, butane—0.40, butene-1—81.49, butene-2—0.54, hexenes—5.67, the solvent—2.03.

EXAMPLE 17

Butene-1 is produced in a manner similar to that of the foregoing Example 16, except that dioxane is added in the ratio of 3 moles per mole of $Al(i-C_4H_9)_3$. After the distillation the composition of the distillate is the following, %: ethylene—9.96, butane—0.44, butene-1—81.70, butene-2—0.30, hexenes—5.51, the solvent—2.09.

EXAMPLE 18

Butene-1 is produced as in Example 1, except that into the reaction mass withdrawn from the reactor dimethylformamide is introduced in the ratio of 0.25 mole per mole of $Al(C_2H_5)_3$. After the distillation the distillate has the following composition, %: ethylene—10.0, butane—0.40, butene-1—81.67, butene-2—0.35, hexenes—5.58, the solvent—2.00.

EXAMPLE 19

Butene-1 is produced as in Example 1, except that dimethylformamide is introduced in the ratio of 3 moles per mole of $Al(i-C_4H_9)_3$. The resulting distillate has the following composition, %: ethylene—9.98, butane—0.44, butene-1—81.80, butene-2—0.1, hexenes—5.56, the solvent—2.12.

EXAMPLE 20

Butene-1 is produced as in Example 1, except that into the reaction mass discharged from the reactor methylethylketone is introduced in the ratio of 1 mole per mole of $Al(C_2H_5)_3$. The resulting distillate has the following composition, %: ethylene—10.01, butane—0.42, butene-1—81.6, butene-2—0.4, hexenes—5.56, the solvent—2.00.

EXAMPLE 21

Butene-1 is produced as in Example 1, except that methyethylketone is added in the ratio of 3 moles per mole of $Al(i-C_4H_9)_3$. The resulting distillate has the following composition, %: ethylene—10.3, butane—0.43, butene-1—81.77, butene-2—0.25, hexenes—5.18, the solvent—2.07.

EXAMPLE 22

Butene-1 is produced in a manner similar to that described in Example 1, except that as the solvent use is made of heptane and as the modifying agent—acetone. After the distillation the distillate has the following composition, %: ethylene—11.57, butane—0.40, butene-1—81.75, butene-2—0.25, hexenes—5.08, the solvent—0.95.

EXAMPLE 23

Butene-1 is produced as in Example 1, except that as the solvent use is made of the hexane fraction, while the modifying agent is acetone. After the distillation the composition of the distillate is the following, %: ethylene—11.27, butane—0.41, butene-1—81.78, butene-2—0.22, hexenes—5.07, the solvent—1.25.

EXAMPLE 24

Butene-1 is produced as in Example 1, except that into the reaction mass withdrawn from the reactor isoamyl alcohol is introduced. The distillate has the following composition after the distillation, %: ethylene—9.94, butane—0.40, butene-1—81.58, butene-2—0.30, hexenes—5.77, the solvent—2.01.

EXAMPLE 25

Butene-1 is produced as in Example 15, except that into the reaction mass withdrawn from the reactor diethyl ether is introduced. After the distillation the distilled has the following composition, %: ethylene—10.02, butane—0.43, butene—81.30, butene-2—0.45, hexenes—5.62, the solvent—2.00.

EXAMPLE 26

Butene-1 is produced in a manner similar to that described in Example 15, except that into the reaction mass tetrahydrofuran is introduced. After the distillation the composition of the distillate is the following, %: ethylene—10.0, butane—0.40, butene-1—81.71, butene-2—0.29, hexenes—5.58, the solvent—2.02.

TABLE 1

| Examples 1 | Components, % by mass | | | | | Solvent 7 | Modifying agent 8 | Molar ratio of modifier to $AlR_3$ 9 |
|---|---|---|---|---|---|---|---|---|
| | ethylene 2 | butane 3 | butene-1 4 | butene-2 5 | hexenes 6 | | | |
| 2 | 10.3 | 0.40 | 80.7 | 0.67 | 5.7 | 2.33 | Methyl-ethyl-ketone | 0.5:1 |
| 3 | 10.7 | 0.44 | 31.2 | 0.20 | 5.4 | 1.80 | Methyl-ethyl-ketone | 5:1 |
| 4 | 11.0 | 0.46 | 81.9 | 0.28 | 5.7 | 0.66 | Methyl-ethyl-ketone | 7:1 |
| 5 | 10.5 | 0.41 | 81.6 | 0.75 | 5.6 | 1.09 | Isoamyl alcohol | 0.4:1 |
| 6 | 10.4 | 0.43 | 21.8 | 0.25 | 5.4 | 1.72 | Isoamyl alcohol | 6:1 |
| 7 | 10.3 | 0.42 | 81.6 | 0.70 | 5.5 | 1.48 | Diethylene glycol | 0.7:1 |
| 8 | 12.0 | 0.35 | 81.1 | 0.55 | 4.9 | 1.10 | Ethylene glycol | 4:1 |
| 9 | 11.1 | 0.30 | 80.5 | 0.40 | 4.9 | 2.75 | Acetamide | 2:1 |
| 10 | 11.4 | 0.35 | 80.9 | 0.70 | 5.1 | 1.55 | Benzamide | 0.3:1 |

INDUSTRIAL APPLICABILITY

The present invention is useful in the production of polybutene, a copolymer of ethylene and butene-1, methylethylketone, acetic acid, maleic anhydride, ethylene oxide using butene-1 as the starting feedstock.

We claim:

1. A process for producing butene-1 comprising dimerization of ethylene in the presence of a catalytical system: titanium tetraalkoxide-aluminium trialkyl in a hydrocarbon solvent, followed by rectification of the reaction mass in the presence of a modifying agent, characterized in that as the modifying agent use is made of a compound selected from the group consisting aliphatic mono- or dihydric alcohols, aliphatic ethers or cyclic ethers, aliphatic ketones, amides of carboxylic acids.

2. A process according to claim 1, characterized in that upon using aliphatic mono- or dihydric alcohols, aliphatic ethers, cyclic ethers or, aliphatic ketones as the modifying agent, the rectification is conducted at a molar ratio of the modifying agent to aluminium trialkyl of the catalytical system equal to 1-3.

3. A process according to claim 1, characterized in that upon using amides of carboxylic acids as the modifying agent, the rectification is conducted at a molar ratio of the modifying agent to aluminium trialkyl of the catalytical system equal to 0.25-3.00.

* * * * *